(12) United States Patent
Inoue

(10) Patent No.: US 10,441,146 B2
(45) Date of Patent: Oct. 15, 2019

(54) METHOD OF MEASURING DISTANCE BY AN ENDOSCOPE, AND ENDOSCOPE SYSTEM

(71) Applicant: OLYMPUS CORPORATION, Tokyo (JP)

(72) Inventor: Shintaro Inoue, Tokyo (JP)

(73) Assignee: Olympus Corporation, Tokyo (JP)

( * ) Notice: Subject to any disclaimer, the term of this patent is extended or adjusted under 35 U.S.C. 154(b) by 329 days.

(21) Appl. No.: 15/191,685

(22) Filed: Jun. 24, 2016

(65) Prior Publication Data

US 2016/0302653 A1   Oct. 20, 2016

Related U.S. Application Data

(63) Continuation of application No. PCT/JP2014/080347, filed on Nov. 17, 2014.

(30) Foreign Application Priority Data

Dec. 26, 2013   (JP) ................................ 2013-269274

(51) Int. Cl.
*A61B 1/045* (2006.01)
*A61B 5/107* (2006.01)
(Continued)

(52) U.S. Cl.
CPC .......... *A61B 1/045* (2013.01); *A61B 1/00006* (2013.01); *A61B 1/00009* (2013.01);
(Continued)

(58) Field of Classification Search
CPC ............ A61B 1/00006; A61B 1/00009; A61B 1/00147; A61B 1/0016; A61B 1/0051;
(Continued)

(56) References Cited

U.S. PATENT DOCUMENTS 4,895,431 A    1/1990  Tsujiuchi et al.
5,159,446 A *  10/1992 Hibino ............... A61B 1/00039
                                                    348/65

(Continued)

FOREIGN PATENT DOCUMENTS

JP      S63-246716 A     10/1988
JP      H03-080824 A      4/1991
(Continued)

OTHER PUBLICATIONS

International Search Report dated Feb. 10, 2015 issued in PCT/JP2014/080347.
(Continued)

*Primary Examiner* — Aaron B Fairchild
(74) *Attorney, Agent, or Firm* — Scully Scott Murphy & Presser, P.C.

(57) ABSTRACT

A method of measuring distance by an endoscope includes a step of imaging and a step of measuring distance. the step of imaging includes a step of producing out an image taken by an imaging unit. The step of measuring distance includes a step of moving the axis of sighting of the imaging unit and a step of computing a distance to a subject of interest on the basis of a first image taken before the step of moving, a second image taken during the step of moving and the amount of distance-measurement control.

4 Claims, 18 Drawing Sheets

(51) Int. Cl.
| | | |
|---|---|---|
| *G06T 7/00* | (2017.01) | |
| *G06T 7/593* | (2017.01) | |
| *H04N 13/207* | (2018.01) | |
| *H04N 13/221* | (2018.01) | |
| *H04N 13/211* | (2018.01) | |
| *G01C 3/08* | (2006.01) | |
| *A61B 1/00* | (2006.01) | |
| *A61B 1/005* | (2006.01) | |
| *A61B 34/20* | (2016.01) | |
| *A61B 5/00* | (2006.01) | |
| *H04N 13/00* | (2018.01) | |
| *A61B 1/313* | (2006.01) | |
| *A61B 5/06* | (2006.01) | |
| *A61B 17/34* | (2006.01) | |
| *A61B 90/50* | (2016.01) | |
| *A61B 90/00* | (2016.01) | |

(52) U.S. Cl.
CPC ........ *A61B 1/0051* (2013.01); *A61B 1/00147* (2013.01); *A61B 1/00172* (2013.01); *A61B 5/1076* (2013.01); *A61B 5/1079* (2013.01); *A61B 5/6847* (2013.01); *A61B 34/20* (2016.02); *G01C 3/08* (2013.01); *G06T 7/0012* (2013.01); *G06T 7/593* (2017.01); *H04N 13/207* (2018.05); *H04N 13/211* (2018.05); *H04N 13/221* (2018.05); *A61B 1/0016* (2013.01); *A61B 1/3132* (2013.01); *A61B 5/061* (2013.01); *A61B 17/3421* (2013.01); *A61B 90/50* (2016.02); *A61B 2017/347* (2013.01); *A61B 2034/2048* (2016.02); *A61B 2090/061* (2016.02); *A61B 2090/062* (2016.02); *A61B 2090/0811* (2016.02); *G06T 2207/10028* (2013.01); *H04N 2013/0081* (2013.01)

(58) Field of Classification Search
CPC . A61B 1/045; A61B 5/1076; A61B 2090/061; A61B 2090/0811; A61B 1/00043; A61B 5/06; A61B 5/062; A61B 5/065; A61B 5/066; A61B 34/20; A61B 5/1079; A61B 1/00193; G01B 11/22; G06T 2207/10028; G04N 13/207; G04N 13/211; G04N 13/221; G04N 2013/0081
USPC ........................................ 600/117, 118, 146
See application file for complete search history.

(56) References Cited

U.S. PATENT DOCUMENTS

| | | | |
|---|---|---|---|
| 5,253,647 A * | 10/1993 | Takahashi | A61B 5/065 600/117 |
| 5,347,987 A * | 9/1994 | Feldstein | A61B 1/00147 348/65 |
| 5,432,543 A | 7/1995 | Hasegawa et al. | |
| 2002/0022765 A1* | 2/2002 | Belson | A61B 1/0053 600/146 |
| 2003/0045778 A1* | 3/2003 | Ohline | A61B 1/0053 600/114 |
| 2003/0151659 A1 | 8/2003 | Kawano et al. | |
| 2006/0239539 A1 | 10/2006 | Kochi et al. | |
| 2007/0015967 A1* | 1/2007 | Boulais | A61B 1/0005 600/146 |
| 2011/0261165 A1 | 10/2011 | Kochi et al. | |

FOREIGN PATENT DOCUMENTS

| | | |
|---|---|---|
| JP | 5-49599 | 3/1993 |
| JP | H06-007289 A | 1/1994 |
| JP | 3041420 B1 | 5/2000 |
| JP | 2000-210248 A | 8/2000 |
| JP | 2006-003280 A | 1/2006 |

OTHER PUBLICATIONS

Extended Supplementary European Search Report dated Sep. 22, 2017 received in 14874391.7.

* cited by examiner

FIG.1
FIG.2
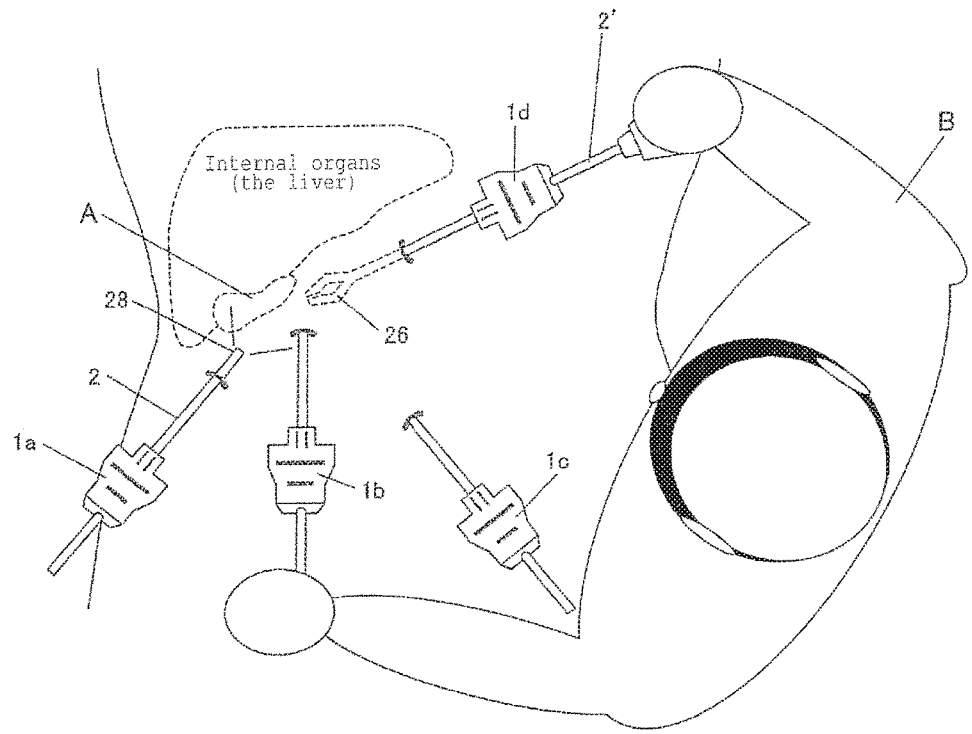
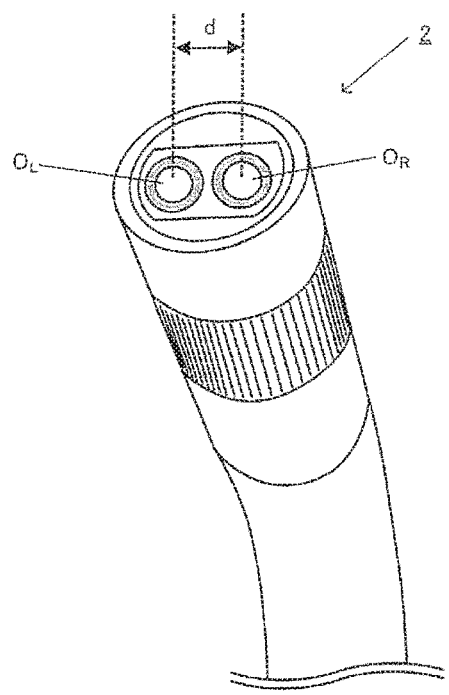

FIG.6A
FIG.6B
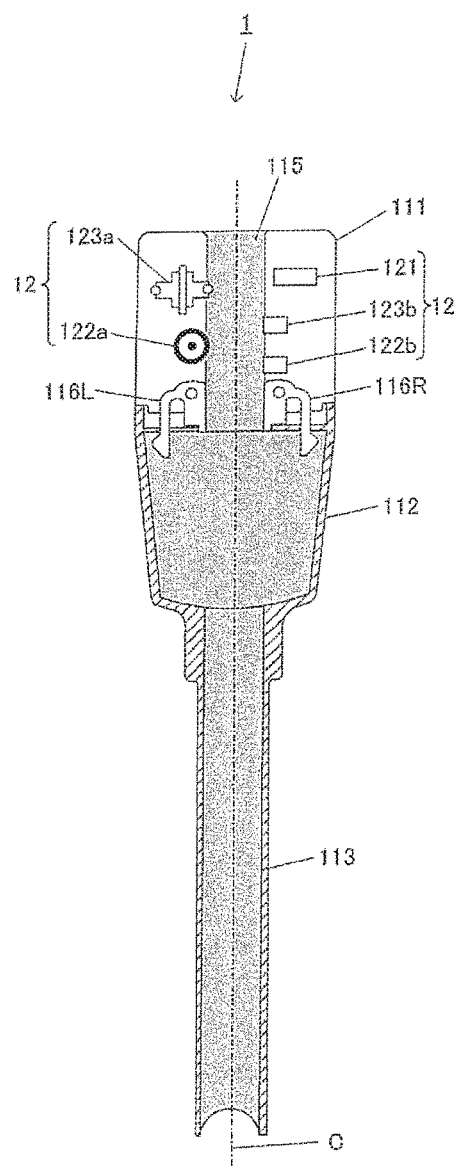
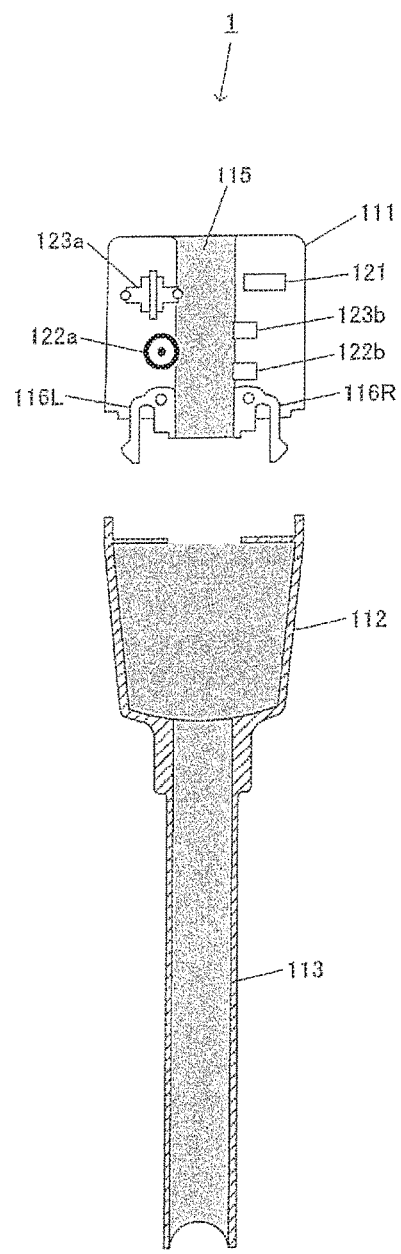

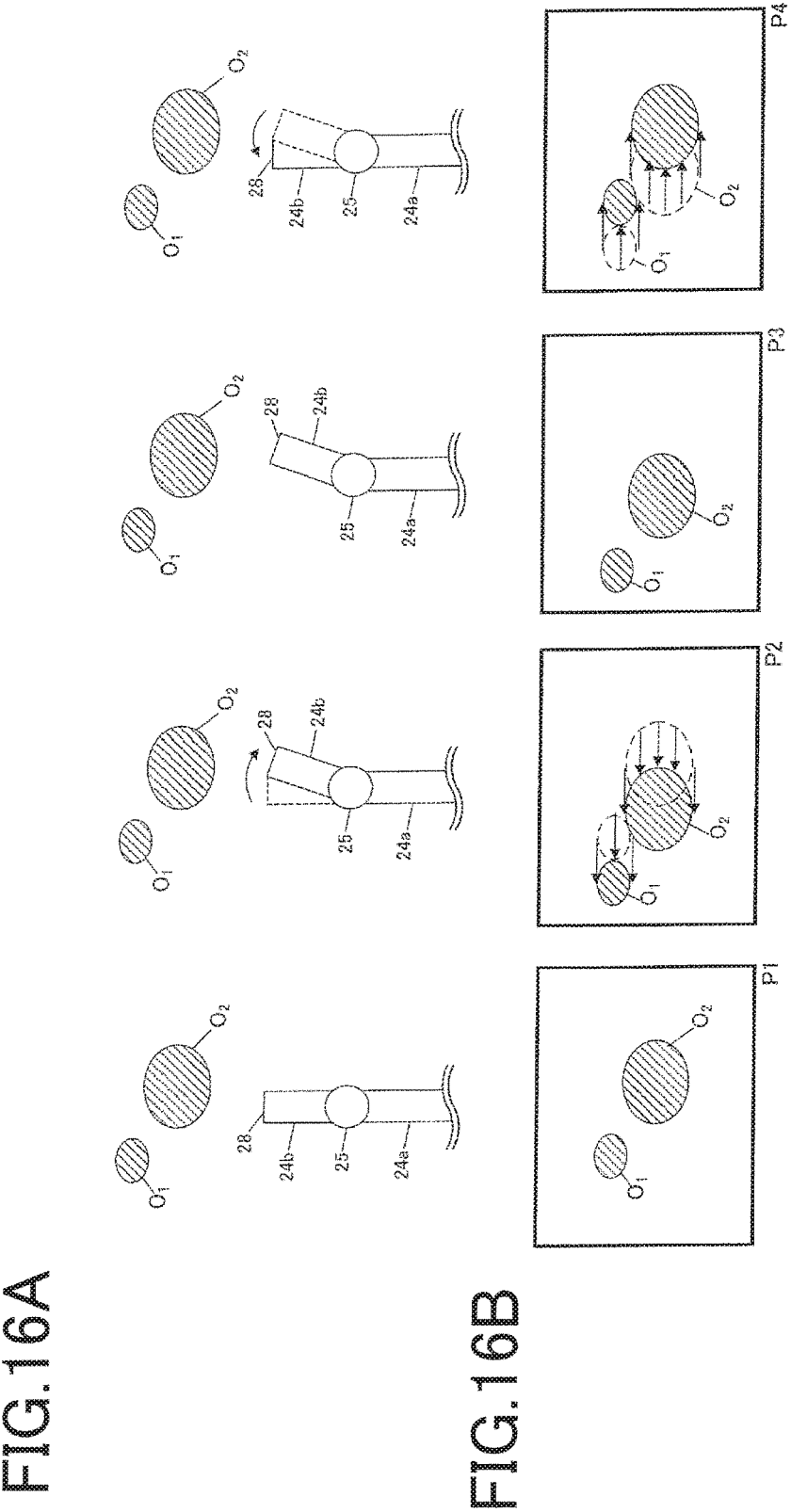

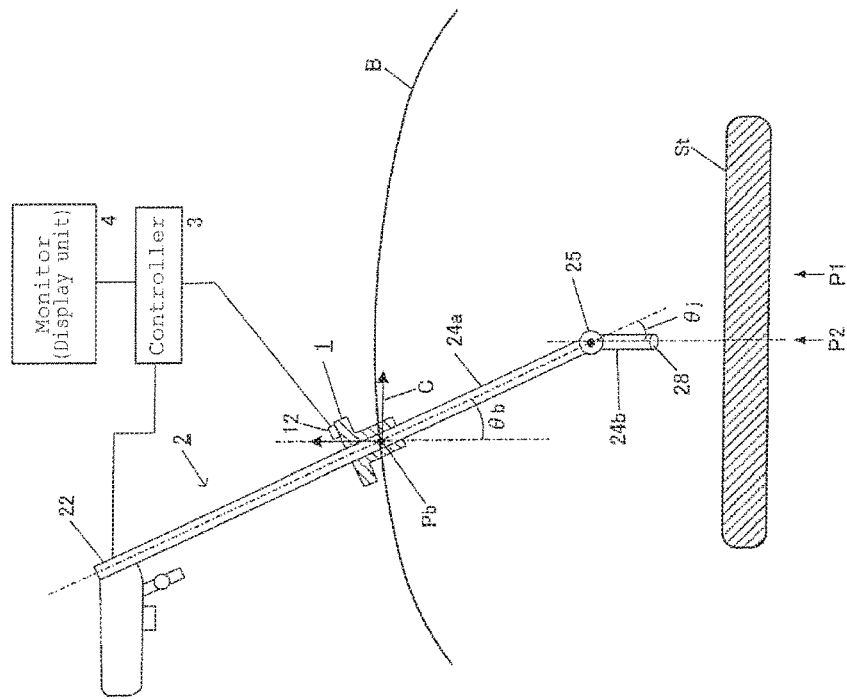
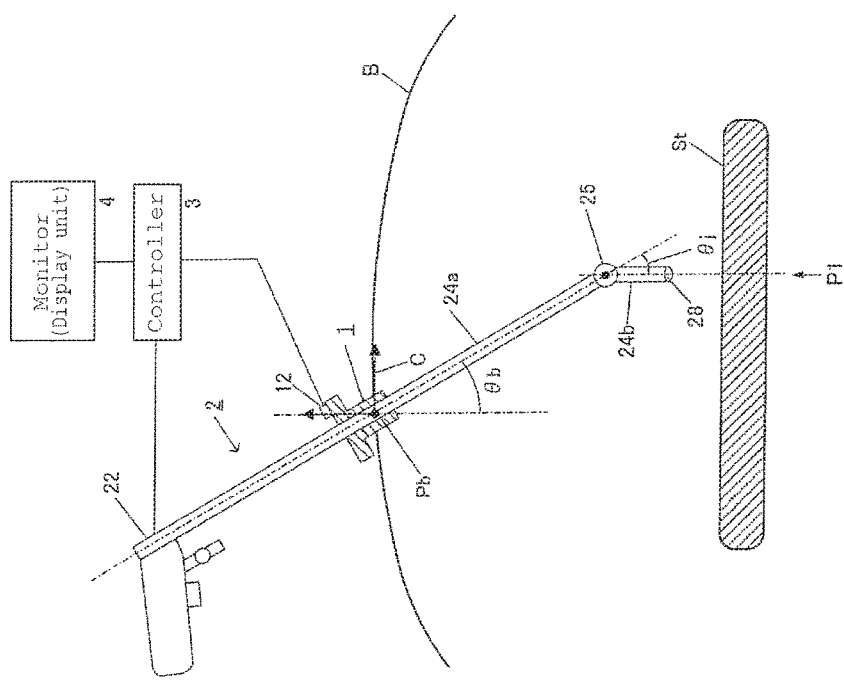

METHOD OF MEASURING DISTANCE BY AN ENDOSCOPE, AND ENDOSCOPE SYSTEM

CROSS-REFERENCE TO RELATED APPLICATIONS

This application is a continuation claiming priority on the basis of Japan Patent Application No. 2013-269274 applied in Japan on Dec. 26, 2013 and based on PCT/JP2014/080347 filed on Nov. 17, 2014. The contents of both the PCT application and the Japan Application are incorporated herein by reference.

BACKGROUND OF THE INVENTION AND RELATED ART STATEMENT

The present invention relates to a method of measuring distance by an endoscope that is inserted through the body of a patient for surgical operation to view the interior of the patient's body as well as an endoscope system.

Currently, a trocar is inserted from the body surface of a patient through the interior of the body and various medical instruments are inserted through the trocar to carry out laparoscopic surgery for various treatments and medical examinations in the interior of the body. Although this laparoscopic surgery is less invasive of patients because of making do with a limited incision in the body surface of the patient, it is still required to improve on the visibility of an endoscope and the operability of medical instruments because of the need for performing operations while viewing the interior of the patient's body by way of the endoscope. For laparoscopic surgery, it is required to check up on the interior states of the patient's body with images from the endoscope, and distance measurement is implemented by the endoscope as one method of obtaining detailed information from such images.

Japanese Patent Publication JP(A)3-80824 discloses an endoscope apparatus for measuring the amount of insertion of an endoscope to measure a distance between the endoscope and a subject of interest from a feature point position of the subject on the images before and after insertion.

Japanese Patent No. 3041420 discloses an endoscope system for measuring the amount of movement of an endoscope to compare an image before movement with an image after movement for distance measurement.

SUMMARY OF INVENTION

In the present embodiment, a method of measuring distance by an endoscope includes the step of
imaging, measuring distance, and changing the step of imaging and the step of measuring distance,
wherein the step of imaging includes
moving the axis of sighting of the imaging unit by controlling the moving joint on the basis of an direction instruction from an input unit,
and
producing out an image taken by the imaging unit, and
wherein the step of measuring distance includes
moving the axis of sighting of the imaging unit by controlling the moving joint on the basis of an amount of distance-measurement control,
acquiring a first image taken before the step of moving on the basis of an amount of distance-measurement control and a second image taken during the step of moving on the basis of an amount of distance-measurement control, and
computing a distance to a subject of interest on the basis of the first image, the second image and the amount of distance-measurement control.

A method of measuring distance by an endoscope comprising the step of:
imaging by following-up and measuring distance, wherein:
wherein the step of imaging by following-up comprises controlling the moving joint such that the axis of sighting of the imaging unit has a given angle with respect to a preset follow-up reference surface,
producing out an image taken by the imaging unit, and
wherein the step of measuring distance comprises
computing a distance to a subject of interest by making use of a first image and a second image taken during the step of imaging by following-up, and an amount of movement of the endoscope between a point of time when the first image is taken and a point of time when the second image is taken.

Further, the present embodiment provides an endoscope system, including
an imaging unit configured to be capable of acquiring an image;
a moving joint configured to make an axis of sighting of the imaging unit movable;
an input unit configured to be capable of entering an instruction about a direction of the moving joint; and
a control unit configured to be capable of changeably implementing an imaging processing and a distance-measurement processing;
wherein the imaging processing configured to controls the moving joint on the basis of the direction instruction from the input unit to move the axis of sighting of the imaging unit and produce out an image taken by the imaging unit;
wherein the distance-measurement processing configured to control the moving joint on the basis of an amount of distance-measurement control to implement a movement processing for moving the axis of sighting of the imaging unit, and acquire a first image taken before implementation of the movement processing and a second image taken during implementation of the movement processing so that a distance to a subject of interest is computed on the basis of the first image, the second image and the amount of distance-measurement control.

BRIEF DESCRIPTION OF DRAWINGS

FIG. 1 is illustrative of how to carry out laparoscopic surgery using medical instruments (such as an endoscope and forceps).

FIG. 2 shows one illustrative state of the distal end of a compound-eye endoscope.

FIGS. 6A and 6B are illustrative of the internal construction of the trocar according to one embodiment of the invention.

FIGS. 16A and 16B are illustrative of how to determine images for distance measurement according to one embodiment of the invention.

FIGS. 20A and 20B are illustrative of distance-measurement processing that is implemented upon follow-up imaging processing according to one embodiment of the invention.

DESCRIPTION OF EMBODIMENTS

Figure 3:
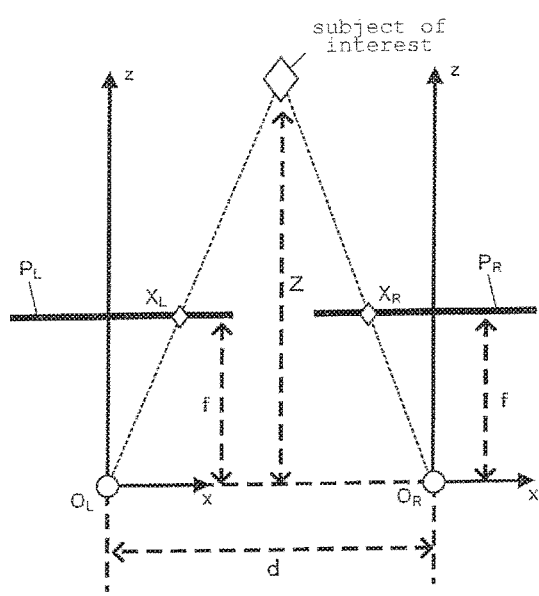
FIG. 3 is illustrative of the principle of stereoscopic measurement using a compound-eye endoscope.

FIG. 1 is illustrative of how to carry out laparoscopic surgery using various medical instruments. In laparoscopic surgery, there are plural holes cut open in the abdomen or the like of a patient. Then, various medical instruments such as an endoscope 2, forceps 2' and (electric) scalpels are inserted through the patient's body for viewing and treatment of an affected site A while checking up on images taken through the endoscope 2. This laparoscopic surgery is less invasive of patients because of requiring less incision area.

In laparoscopic surgery, tubes called trocars (channels) 1a to 1d are inserted in openings cut open in the patient's body wall, and various medical instruments are inserted through the patient via the trocars 1a to 1d. FIG. 1 illustrates that the endoscope 2 is being inserted through the trocar 1a while the forceps 2' are being inserted through the trocar 1d. On the distal end part of the endoscope 2, there is an imaging unit 28 mounted to show images taken by the imaging unit 28 on a display unit such as a monitor. Usually, the endoscope 2 is manipulated by an assistant called the "scopist", and the subject of interest is imaged on the basis of an instruction from a surgeon B. The forceps 2' are provided at the distal end part with a distal-end gripper 26 that works as an end effector, and the surgeon B (user) manipulates the forceps 2' to open or close or otherwise handle the distal-end gripper 26 for surgical operation of the affected site A. With laparoscopic surgery, it is thus possible for the surgeon B to use the forceps 2' for surgical operation while viewing images taken through the endoscope 2.

In such laparoscopic surgery, distance measurement is often carried out so as to get a more precise grasp of what is going on in the interior of the patient's body. Distance measurement may be implemented by various methods, one of which makes use of a compound-eye endoscope, viz., an endoscope having two imaging units so as to measure a distance from the distal end of the endoscope to a subject of interest pursuant to the stereoscopic measurement principle. FIG. 2 shows one specific state of the distal end of such a compound-eye endoscope 2. The compound-eye endoscope 2 includes two imaging units OL and OR on its distal end part at a distance d (parallax) between them. With the compound-eye endoscope 2, it is possible not only to measure a distance to the subject of interest but also to obtain a three-dimensional viewing of the subject of interest.

FIG. 3 is illustrative of the principle of stereoscopic measurement using the compound-eye endoscope 2. Here take the axis of sighting of the compound-eye endoscope 2 as the z-axis, and an axis orthogonal thereto as the xy-plane (with the y-axis left out of here). The subject of interest imaged through the imaging units OL and OR (focal length f) will be put in positions XL and XR on images PL and PR. Here take the distance (parallax) between both the imaging units OL and OR as d. A distance Z from the compound-eye endoscope 2 to the subject of interest may be computed from Equation (1) according the principle of triangulation.

$$Z = d \cdot f / (XL - XR) \quad (1)$$

By use of the images PL and PR taken through the compound-eye endoscope 2 including the two imaging units OL and OR at its distal end, it is thus possible to compute a distance to the subject of interest at a suitable place in the taken images. However, such compound-eye endoscope 2 must have two imaging units OL and OR mounted at its distal end, resulting in an increase in its diameter. Unlike such a conventional distance measurement method, the present invention relates to distance measurement using a monocular (single imaging unit) endoscope.

Figure 4A:
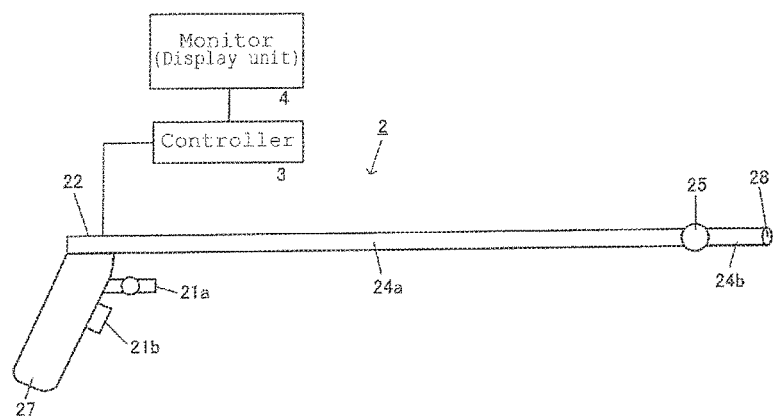
FIGS. 4A and 4B are illustrative of the construction and control configuration of the endoscope according to one embodiment of the invention.
Figure 4B:
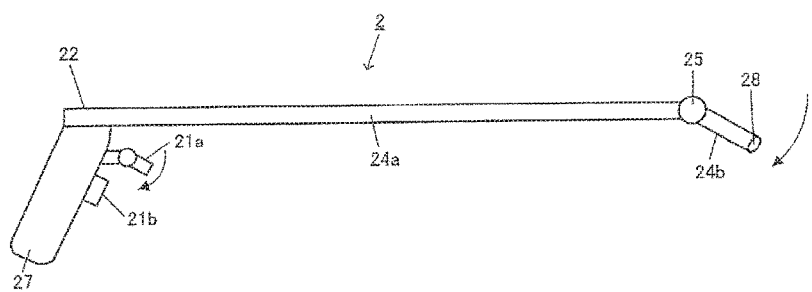

FIGS. 4A and 4B are illustrative of the construction and control configuration of the endoscope according to one embodiment of the invention. FIG. 4A shows how the endoscope 2 is connected to a controller 3. The same goes for FIG. 4B with the exception that the controller 3 is not shown. The endoscope 2 serving as a medical instrument includes a first shaft 24 connected to the gripper member 27 and a second shaft 24b that is rotationally connected to the first shaft 24a by way of a moving joint 25. The distal end of the second shaft 24b is provided with the imaging unit 28 serving as an end effector. In the embodiment described herein, a single (monocular) imaging unit 28 is used. An image taken by the imaging unit 28 is produced out to the controller 3, and the surgeon may operate a display unit such as a monitor 4 to display the image on it, thereby viewing what is going on in the patient's body.

The gripper member 27 is provided with a direction input part 21a and a distance-measurement instruction part 21b, by which the surgeon may adjust the direction (of the axis of sighting) of the imaging unit 28 and give an instruction about distance measurement. As depicted in FIG. 4B, a driver 22 is driven on the basis of operation of the direction input part 21a. The amount of driving by the driver 22 is transmitted by way of a wire or other means to the moving joint 25 for its rotation. The imaging direction (of the axis of sighting) of the imaging unit 28 provided at the distal end of the second shaft 24b is adjusted on the basis of the rotation of the moving joint 25. While the moving joint 25 is shown in the form of two-dimensional operation on the sheet plane, it is to be understood that it may be operated in three-dimensional directions including a direction orthogonal to the sheet plane.

Figure 7:
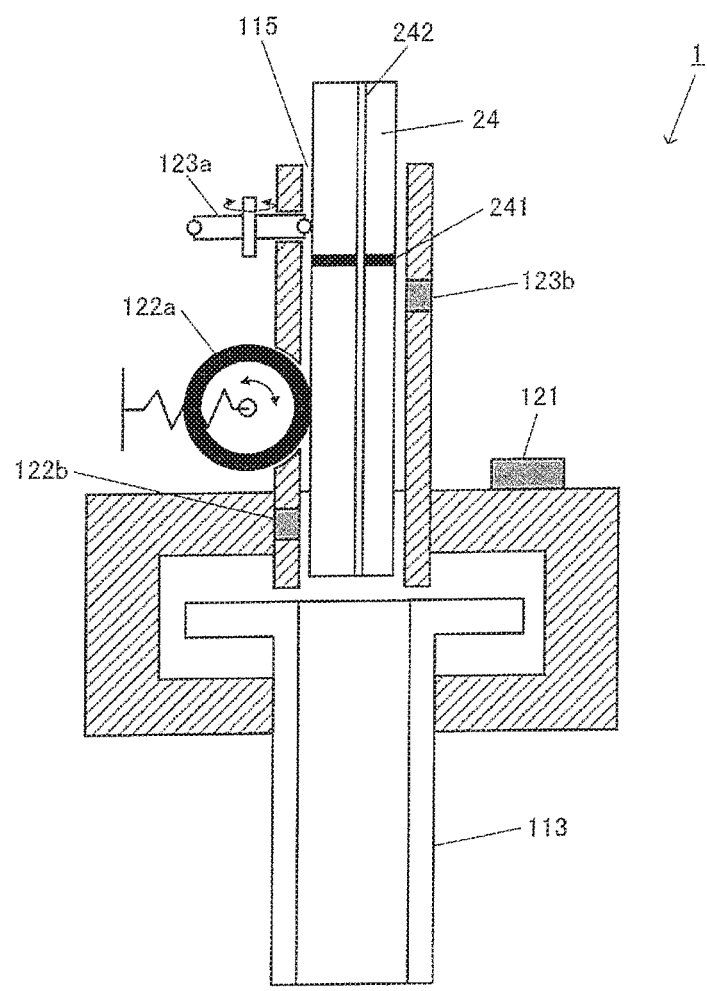
FIG. 7 is illustrative in schematic of the construction of the trocar sensor according to one embodiment of the invention.

Insertion of the endoscope 2 as explained above through the trocar 1 that communicates the patient's body surface with the interior of the body makes it possible to view the interior of the body in laparoscopic surgery. In a certain aspect of the embodiment described herein, medical instruments such as endoscope 2 are used in states detected by various sensors that are included in the trocar 1. For this reason, the construction of the trocar 1 including various sensors is illustrated in FIGS. 5, 6 and 7.

Figure 5:
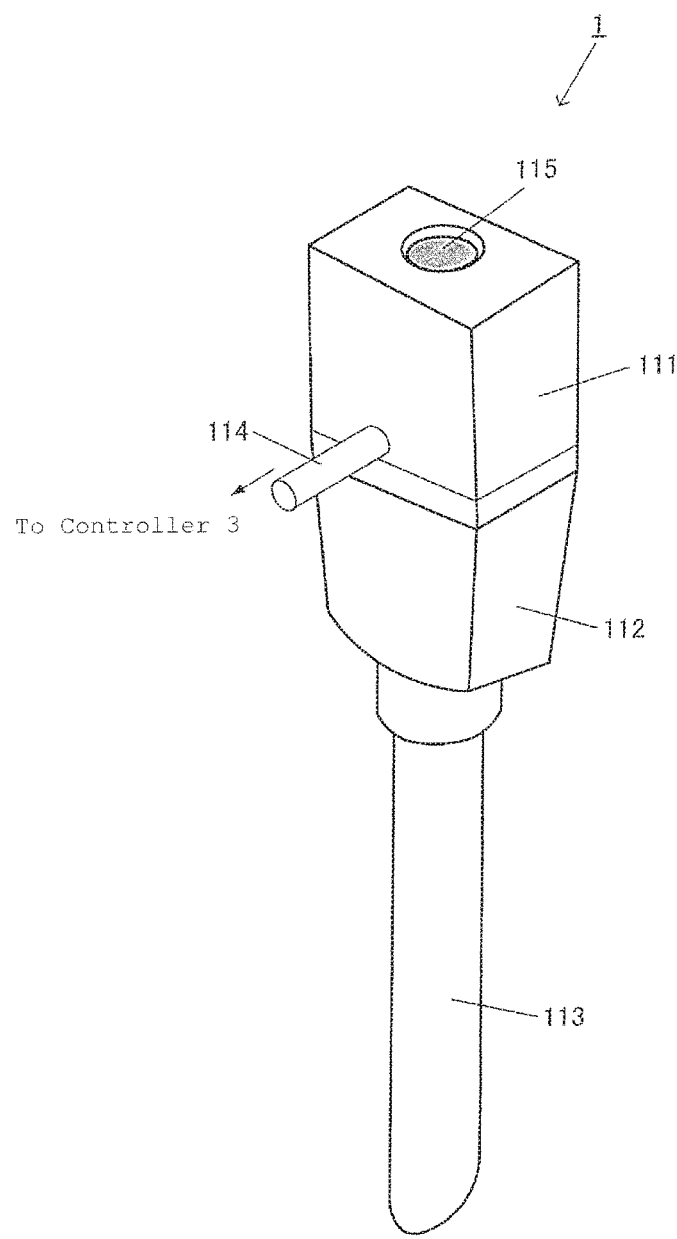
FIG. 5 is illustrative of the external appearance of the trocar according to one embodiment of the invention.

FIG. 5 is illustrative of the external appearance of the trocar 1 that may be used with the medical system according to one embodiment of the invention. The trocar 1 described herein includes an upper housing 111, a lower housing 112 and a cylindrical tube 113. The upper housing 111 is provided with an insertion path 115 for insertion of various medical instruments. The cylindrical tube 113 is inserted through the patient's body. A medical instrument inserted from the insertion path 115 goes through the lower housing 112 and cylindrical tube 113, and is inserted from the lower end of the cylindrical tube 113 into the patient's body for the purpose of viewing the interior of the patient's body or surgical treatments in the patient's body.

Within the upper housing 111 there are various sensors provided for detection of the states of the trocar 1 and the medical instrument inserted from the insertion path 115. Signals produced out of various sensors are sent out to the controller 3 by way of a cable 114. Note here that the cable 114 has another function of feeding power supply to various sensors. While communication between the sensors and the controller 3 may be of such a wired type, it is to be understood that use of wireless communication and battery-activated driving may lead to elimination of the cable 114 from the trocar 1.

FIGS. 6A and 6B are sectional views of the internal construction of the trocar 1 according to one embodiment of the invention. While the upper housing 111 is shown to have the insertion path 115 as explained with reference to FIG. 5, it is to be noted that a brown part from the insertion path 115 down to the lower end of the cylindrical tube 113 is a communicating section through which various medical instruments are to be inserted. The upper housing 111 and the lower housing 112 may be coupled to or decoupled from each other by means of coupler members 116R and 116L, each in a clip form. During use of the trocar 1, the upper 111 and lower housing 112 are coupled together as depicted in FIG. 6A, and for cleaning or other purposes, the upper housing 111 may be removed out from the lower housing 112 as depicted in FIG. 6B. This facilitates cleaning, disinfection or replacement of the cylindrical tube 113 as well as maintenance of the upper housing 111 including various sensors. Note here that the trocar 1 may be designed as a single housing in which the upper housing 111 is integral with the lower housing 112.

In the trocar 1 according to the embodiment described herein, the upper housing 111 includes various sensors (for instance, a trocar sensor 12) inside. In the embodiment described herein, the trocar sensor 12 includes a tilt angle detection sensor 121, an amount-of-advanceable/retractable-movement detection sensor 122, and an amount-of-rotation detection sensor 123. The tilt angle detection sensor 121 is provided for detecting the tilt angle of the trocar 1, that is, in which direction the trocar 1 turns with respect to a reference coordinate system. The reference coordinate system here is the one that is defined relative to a fixed object such as a patient or the ground, and various sensors inclusive of an acceleration sensor may be used for the tilt angle detection sensor 121. The acceleration sensor may detect an acceleration applied thereon to detect in which direction the trocar 1 turns, that is, the tilt angle of the trocar 1 with respect to the reference coordinate system.

The amount-of-advanceable/retractable-movement detection sensor 122 is provided for detection of the amount of advanceable/retractable movement of a medical instrument inserted through the trocar 1 in its insertion direction (in the vertical direction in FIGS. 6A and 6B). As already explained with reference to FIG. 1, a surgeon such as a physician inserts or withdraws a medical instrument through the trocar 1 to operate and move the medical instrument within the patient's body to an unerring position. With the amount-of-advanceable/retractable-movement detection sensor 122, it is possible to detect the insertion position of the medical instrument relative to the trocar 1 in the form of the amount of advanceable/retractable movement. FIG. 6A shows the center axis C of the trocar 1 in the insertion direction by a dashed line. The amount-of-advanceable/retractable-movement detection sensor 122 detects the amount of movement parallel with that center axis C in the form of the amount of advanceable/retractable movement. In the embodiment described herein, the amount-of-advanceable/retractable-movement detection sensor 122 is made up of a combined amount-of-advanceable/retractable-movement detection roller 122a and photosensor 122b.

The amount-of-rotation detection sensor 123 is provided for detection of the amount of rotation of a medical instrument that rotates in association with operation as by a surgeon. By rotational operation about the center axis C of a medical instrument inserted through the insertion path 115, it is possible to change the direction of the end effector mounted at the distal end of the medical instrument within the patient's body. The amount-of-rotation detection sensor 123 detects this amount of rotation so that in which direction the end effector of the medical instrument turns can be detected. In the embodiment described herein, the amount-of-rotation detection sensor 123 is made up of a combined amount-of-rotation detection roller 123a and photosensor 123b.

While the internal construction of the trocar 1 has been explained, it is to be understood that the trocar sensor 12 disposed within the trocar 1 sends a detection signal out to the controller 3 by way of a communication unit 13 not shown in FIGS. 6A and 6B. Actuation of the trocar sensor 12 in the embodiment described herein is now explained with reference to FIG. 7 that is a schematic view of the construction of the trocar sensor 12. FIG. 7 is illustrative in schematic of the construction of the trocar sensor 12 disposed within the trocar 1 of FIGS. 6A and 6B, showing that the first shaft 24 of the medical instrument is being inserted through the trocar 1. Note here that FIG. 7 does not show an end effector and so on attached to the distal end of the medical instrument.

There is some margin given to the diameter of the insertion path 115 for the trocar 1 in such a way as to receive the insertion part of the medical instrument such as the first shaft 24. The trocar 1 will be fixed near to the patient's body surface, but it will rotate pivotally with a certain point as reference in association with operation of the medical instrument. The tilt angle detection sensor 121 fixed to the housing of the trocar 1 is capable of detecting pivotal rotation of the trocar 1 to detect the direction of the trocar 1, i.e., the direction of the medical instrument in the reference coordinate system.

In the embodiment described herein, the amount-of-advanceable/retractable-movement detection sensor 122 is made up of a combined amount-of-advanceable/retractable-movement detection roller 122a and photosensor 122b as explained with reference to FIGS. 6A and 6B. The amount-of-advanceable/retractable-movement detection roller 122a has a direction vertical to the plane of FIG. 7 as a rotary axis. This amount-of-advanceable/retractable-movement detection roller 122a is biased by a resilient member like a spring toward the insertion path 115, and comes into contact with the surface of the medical instrument (the first shaft 24) inserted through the insertion path 115 to convert the amount of advanceable/retractable movement of the medical instrument into its amount of rotation. The rotary axis of the amount-of-advanceable/retractable-movement detection roller 122a is provided with an encoder to produce out the amount of rotation of the amount-of-advanceable/retractable-movement detection roller 122a in the form of the amount of advanceable/retractable movement. In the embodiment described herein, the photosensor 122b facing in the insertion path 115 is provided so as to calibrate the amount of advanceable/retractable movement (set it to the initial value). This photosensor 122b is capable of detecting a position-of-advanceable/retractable-movement detection mark 241 positioned on the medical instrument (the first shaft 24 or the like) to calibrate the amount of advanceable/retractable movement detected by the amount-of-advanceable/retractable-movement detection roller 122a. Upon advanceable/retractable movement of the medical instrument through the insertion path 115, therefore, the amount of advanceable/retractable movement will be calibrated (set to the initial value) each time the position-of-advanceable/retractable-movement detection mark 241 is just past the photosensor 122b, making sure detection of the exact amount of advanceable/retractable movement of the medical instrument relative to the trocar 1.

As already explained with reference to FIGS. 6A and 6B, the amount-of-rotation detection sensor 123 according to the embodiment described herein is made up of a combined amount-of-rotation detection roller 123a and photosensor 123b. The amount-of-rotation detection roller 123a has a rotary axis turning in the vertical direction of FIG. 7. This amount-of-rotation detection roller 123a is biased by a resilient member like a spring toward the insertion path 115, and comes into contact with the surface of the medical instrument (the first shaft 24) inserted through the insertion path 115 to convert the amount of rotation of the medical instrument into the amount of rotation of the amount-of-rotation detection roller 123a. Note here that the contact surface of the amount-of-rotation detection roller 123a is preferably provided with a member (like a bearing) that does not interfere with movement of the medical instrument in the insertion direction. The rotary axis of the amount-of-rotation detection roller 123a is provided with an encoder that produces out the amount of rotation of the amount-of-rotation detection roller 123a in the form of the amount of rotation of the medical instrument. In the embodiment described herein, the photosensor 123b facing in the insertion path 115 is provided so as to calibrate the amount of rotation (set it to the initial value). As with the amount-of-advanceable/retractable-movement detection sensor 122, this photosensor 123b is capable of detecting a position-of-rotation detection mark 242 provided on the medical instrument (the first shaft 24 or the like) to calibrate the amount of rotation detected by the amount-of-rotation detection roller 123a.

While the trocar sensor disposed in the trocar 1 has been explained, it is to be understood that various sensor forms may be used to set up the trocar sensor. In the embodiment described herein, for instance, a mechanical sensor using rollers is used for detection of the amount of advanceable/retractable movement or rotation, but an optical sensor used with a laser mouth and capable of detecting the amount and direction of surface movement may also be used for detection of the amount of advanceable/retractable movement or rotation. In that case, the amount of advanceable/retractable movement and rotation may be detected with a single optical sensor. For the medical system according to the embodiment described herein, the direction or the direction and position of the medical instrument inserted through the patient's body are required. In the embodiment described herein, various sensors are mounted in the trocar 1 to detect such parameters so that the trocar 1 is easily handled. It is here to be noted that the direction or the direction and position of the medical instrument may be detected using sensors located outside of the trocar 1. For instance, the tilt angle detection sensor 121 located within the trocar 1 may be mounted directly on the medical instrument side.

Figure 8:
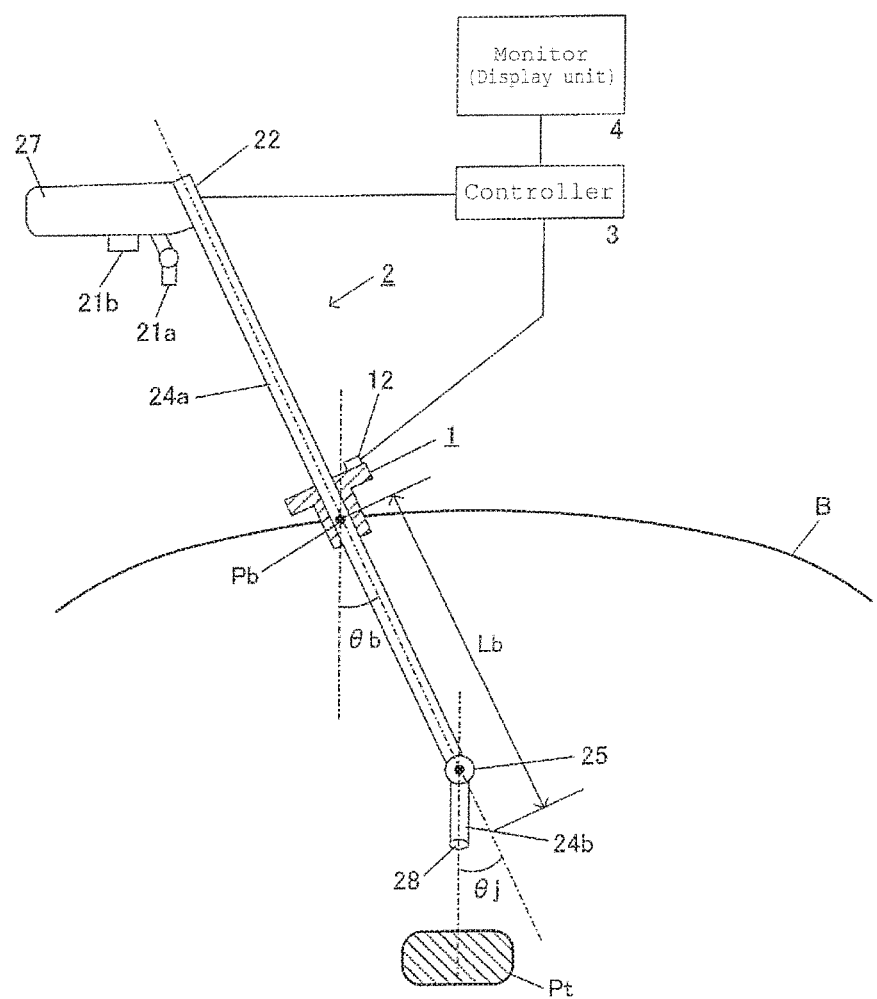
FIG. 8 is illustrative of how the interior of the body is viewed by way of the medical system according to one embodiment of the invention.

FIG. 8 is illustrative of how the interior of the body is viewed by way of the medical system according to one embodiment of the invention. The medical system (endoscope system) explained here is constructed mainly of the aforementioned endoscope 2, trocar 1 and controller 3. In the embodiment described herein, the trocar sensor 12 may be used to detect various states of the endoscope 2 such as its position and amount of movement; however, it is to be noted that the trocar sensor 12 is not always necessary and may be provided as desired.

The trocar 1 is being inserted through the patient's body surface B to communicate the patient's body surface B with the interior of the body by way of the insertion path 115. Through the insertion path 115 in the trocar 1 there is the endoscope 2 inserted so that the interior of the patient's body may be viewed through the imaging unit 28 mounted at the distal end. An image taken by the imaging unit 28 is produced out to the controller 3 where it is displayed on the monitor 4 as a display unit. The direction input part 21a is operated by the operator of the endoscope 2 such as the scopist to rotate the moving joint 25 for variation of the axis of sighting (imaging direction) of the imaging unit 28. The operator may then adjust the position of the gripper member 27 and use the direction input part 21a to vary the axis of sighting of the imaging unit 28 thereby turning the viewing direction toward the subject of interest Pt.

In the embodiment described herein, the position of the gripper member 27 adjusted by the operator may be detected by the trocar sensor 12 as a detection part. Information indicative of the state of the endoscope 2 detected by the trocar sensor 12 is produced out to the controller 3. The trocar sensor 12 is capable of detecting the amount of insertion Lb of the endoscope 2 and the tilt angle θb that the first shaft 24a forms with the reference coordinate system such as a horizontal plane, and the amount-of-rotation detection roller 123a is capable of detecting the angle of rotation of the endoscope 2 or the like. On the basis of the operation of the direction input part 21a, the controller 3 is also capable of detecting the control angle θj of the moving joint 25. With such arrangement it is possible to have a grasp of the state of the endoscope 2. The gripper member 27 is further provided with the distance-measurement instruction part 21b that may be operated by the operator to measure the distance to the subject of interest.

Figure 9:
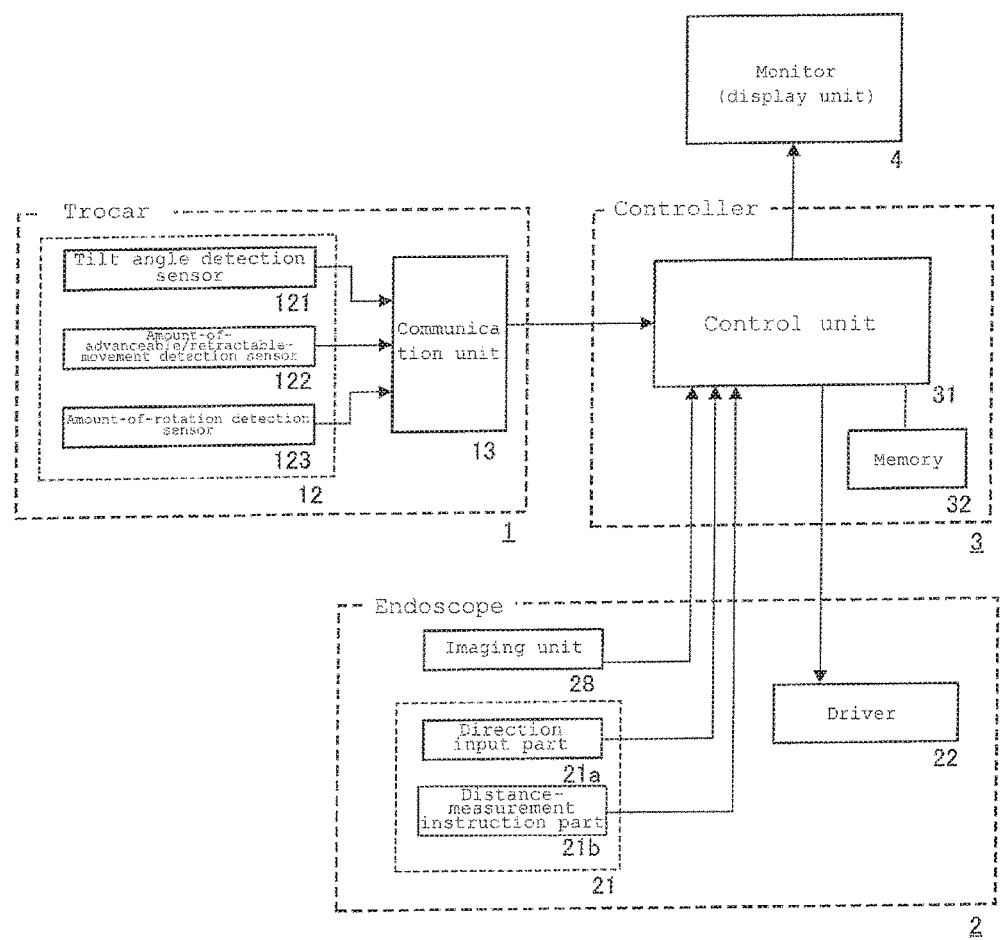
FIG. 9 is a block diagram for the control configuration for the medical system according to one embodiment of the invention.

FIG. 9 is a block diagram for the control configuration of the medical system according to the embodiment described herein. The medical system is constructed mainly of the endoscope 2 and controller 3, and external hardware includes various sensors attached to the trocar 1 and the monitor 4 for displaying an image from the imaging unit 28 on it, and so on.

The trocar 1 includes a trocar sensor 12 including the tilt angle detection sensor 121, amount-of-advanceable/retractable-movement detection sensor 122 and amount-of-rotation detection sensor 123, and a communication unit 13. The endoscope 2 includes an operation input unit 21 including the direction input part 21a explained with reference to FIGS. 4A and 4B, a distance-measurement instruction part 21b and a driver 22. The driver 22 is a member such as a motor for rotation of the moving joint 25 of the endoscope 2. The driver 22 may be designed such that the moving joint 25 is directly rotated or, alternatively, it is indirectly rotated by a wire or thread.

The trocar 1 and endoscope 2 are connected to the controller 3. The controller 3 includes a control unit 31 made up of a CPU and so on, and a memory 32 serving as a storage unit. The memory 32 may store various programs running on the medical system, and various signals and data necessary for running the programs.

Figure 10:
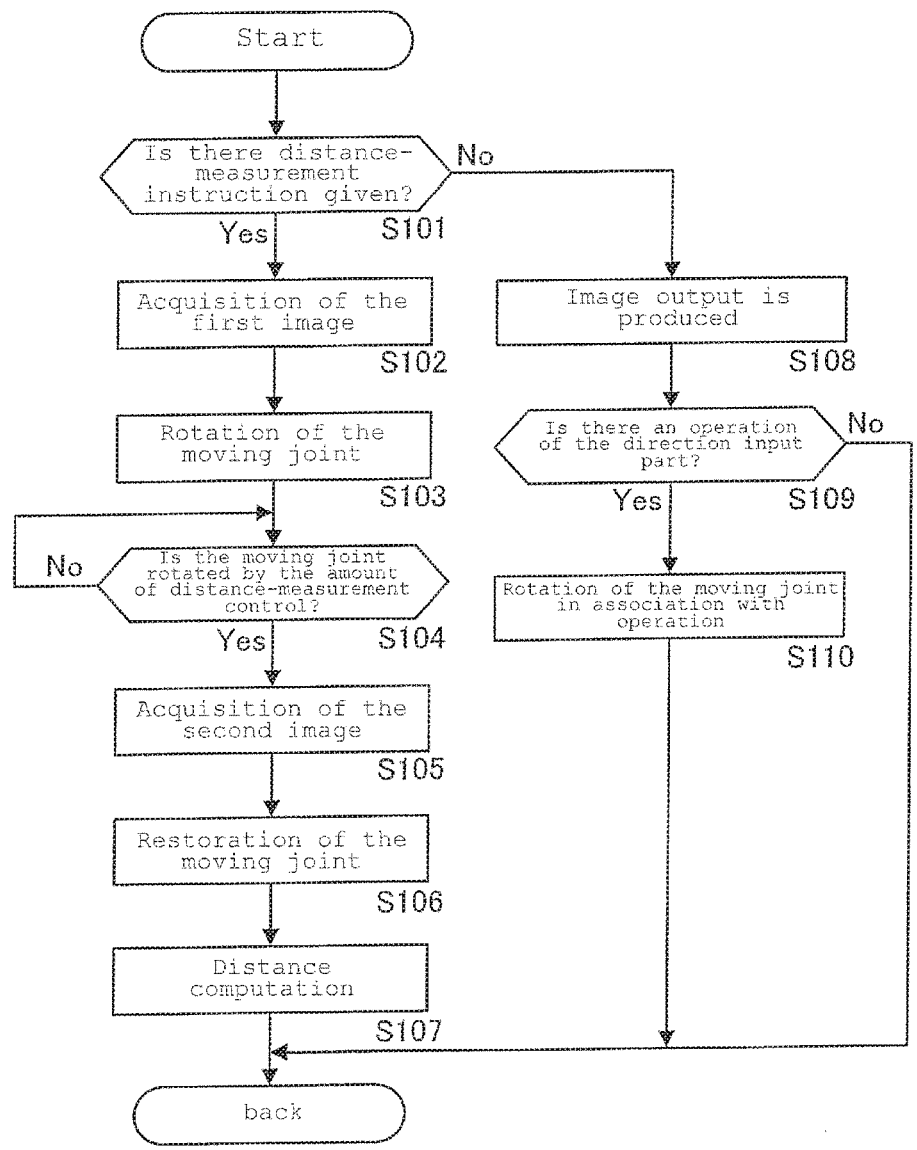
FIG. 10 is a control flowchart for the medical system according to one embodiment of the invention.

How to measure distance using such a medical system (endoscope system) is now explained. FIG. 10 is a control flowchart for the endoscope system according to the embodiment described herein. Processing shown in this control flowchart is implemented on the controller 3 during laparoscopic surgery. As the processing gets started, the controller 3 determines whether or not a distance-measurement instruction is entered from the distance-measurement instruction part 21b (S101). When there is no distance-measurement instruction (S101: No) or, in another parlance, when the endoscope 2 is in a normal processing mode, an image taken by the imaging unit 28 is produced out to the monitor 4 where a screen display is produced (S108). Here when there is an operation (direction instruction) of the direction input part 21a (S109: Yes), there is the moving joint 25 rotated by the driver 22 in association with that operation (S110). Through the processing steps S108 to S110 it is thus possible to view the interior of the patient's body as is the case with the conventional endoscope 2.

Figure 11A:
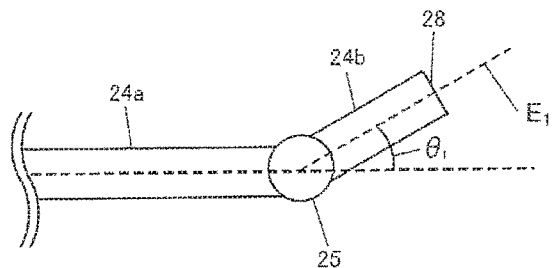
FIGS. 11A and 11B are illustrative of the actuation upon distance measurement of the endoscope according to one embodiment of the invention.
Figure 11B:
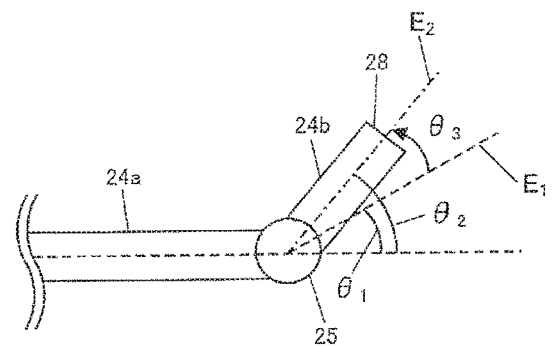

When there is a distance-measurement instruction entered from the distance-measurement instruction part 21b (S101: Yes), on the other hand, distance-measurement processing steps S102 to S107 get started. The operation of the endoscope 2 upon distance measurement is shown in FIGS. 11A and 11B. In the distance-measurement processing, the first image is first taken from the imaging unit 28 (S102). The state of the distal end of the endoscope 2 upon acquisition of the first image is depicted in FIG. 11A showing that the axis of sighting E1 of the imaging unit 28 is tilting at a joint angle θ1 with respect to the center axis of the first shaft 24a. Then, the controller 3 drives the driver 22 on the basis of the preset amount of distance-measurement control to start rotation of the moving joint 25 (S103).

FIG. 11B shows the operation of the endoscope 2 at the time of distance measurement. In this example, the amount of distance-measurement control with respect to the joint angle is set at θ3, and the controller 3 gets the moving joint 25 rotated from the joint angle θ1 to θ2 (θ2=θ1+θ3). The moving joint 25 being placed at the joint angle θ2 is determined on the basis of control of the driver 22 (S104: Yes). That is, when there is the state of FIG. 11B appearing, the controller 3 acquires the second image from the imaging unit 28 (S105), after which there is restoration processing implemented to restore the moving joint 25 back to a state before the start of the distance-measurement processing, i.e., the state of FIG. 11A (S106). During the rotation of the moving joint 25 in the distance-measurement processing step, it is preferable not to produce the image taken by the imaging unit 28 in the form of a screen display on the monitor 4. During the rotation of the moving joint 25 in the distance-measurement processing step, any image fit for the operator's intension is not obtained; an image taken just before the start of the distance-measurement processing is used in place of any image being taken by the imaging unit 28 so that the operator can view the monitor 4 without feeling a sense of discomfort. Thus, if the restoration processing is implemented to restore the imaging unit 28 back to the original state, it is possible to view a succession of images before and after the distance-measurement processing.

In S107, the distance to the subject of interest is computed on the basis of the first image and the second image taken in S102 and S105. The first image and the second image have a parallax for the reason that they are acquired by the rotation of the moving joint 25. For this reason, the first image and the second image may be used to compute the distance to the subject of interest, included in the first image and the second image, in accordance with a principle similar to the stereoscope measurement principle explained with reference to FIG. 3. However, it is preferable that correction for rotation (coordinate system transformation) is carried out because the axis of sighting of the imaging unit 28 has been rotated.

Figure 12:
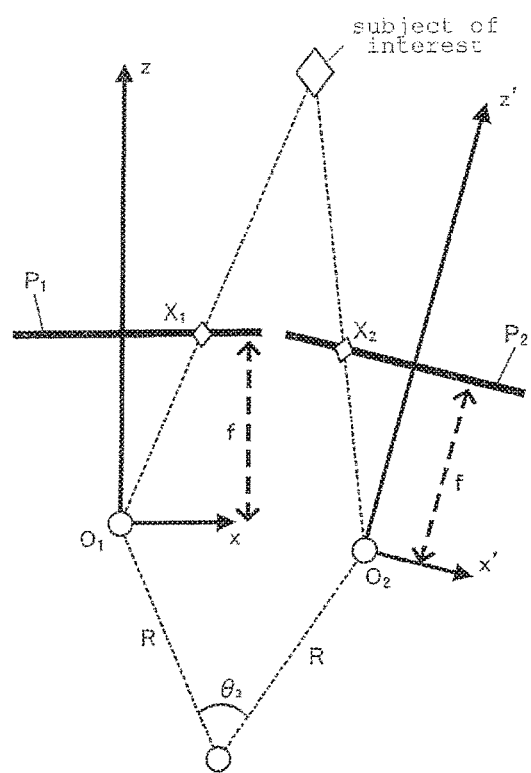
FIG. 12 is illustrative of the principle of pseudo-stereoscopic distance measurement using the endoscope according to one embodiment of the invention.

FIG. 12 shows the pseudo-stereoscopic measurement principle underlying the endoscope according to the embodiment described herein. Suppose now that a coordinate system at the time when the first image P1 is taken is given by xz and a coordinate system at the time when the second image is taken is given by x'z'. The x'z' and xz coordinate systems will tilt by the amount of distance-measurement control θ3. The radius of rotation R, on the other hand, is a value already known from the construction of the endoscope 2 (e.g., positional relations between the moving joint 25 and the imaging unit 28). Therefore, if the amount of distance-measurement control θ3 and radius of rotation R are used for coordinate system transformation for matching the x'z' coordinate system to the xz coordinate system, the distance from the imaging unit 28 to the subject of interest will then be able to be computed on the basis of a principle similar the stereoscopic measurement principle explained with reference to FIG. 3.

The subject of interest may be computed with respect to an appropriate location included in both the first image and the second image. For instance, when the center position of the first image is selected as the location of interest, the computed distance could be displayed as a figure on the image appearing on the display unit 4 through the controller 3. Further, the subject of interest may be selected by the operator or, alternatively, the distances to a plurality of locations of interest may be computed. In that case, the distances could be displayed as contour lines on the images. The computed distance may also be used as proximity warning rather than being displayed. When the computed distance is less than a given value, the monitor 4 or other means such as a speaker may be used to warn that the endoscope is too close to the inner wall in the interior of the body. The measured distance information may also be used for the purpose of varying the control parameters for the moving joint depending on distance. At a near distance, for instance, a coefficient multiplied by the amount of instruction from the direction input part may be made small, and at a far distance, the coefficient may be made large. As a result, the rate of change of the field of view versus input is kept constant even when there is a change in the distance to the subject of interest, resulting likely in improvements in operability.

While the distance-measurement processing steps (S102 to S107) get started on the basis of the distance-measurement instruction entered by the operator, it is to be understood that they may be implemented periodically or automatically in association with a given operation, etc. during use of the endoscope 2; that is, the distance-measurement instruction may be entered not only by the operation of the operator but also from the controller 3.

Figure 13A:
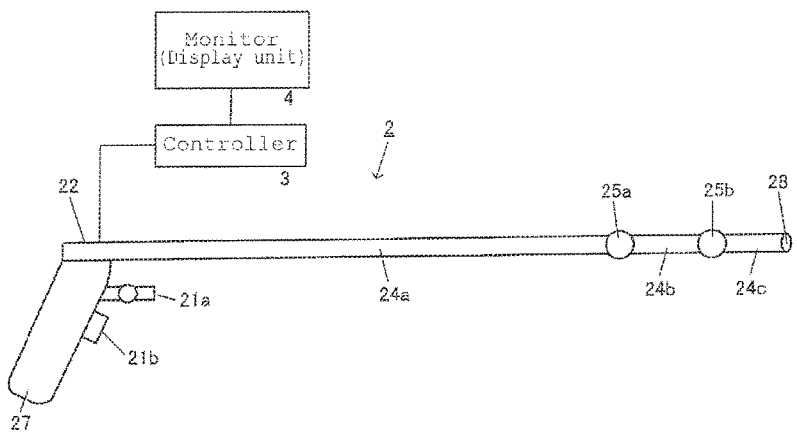
FIGS. 13A and 13B are illustrative of the construction and control configuration of the endoscope according to another embodiment of the invention.
Figure 13B:
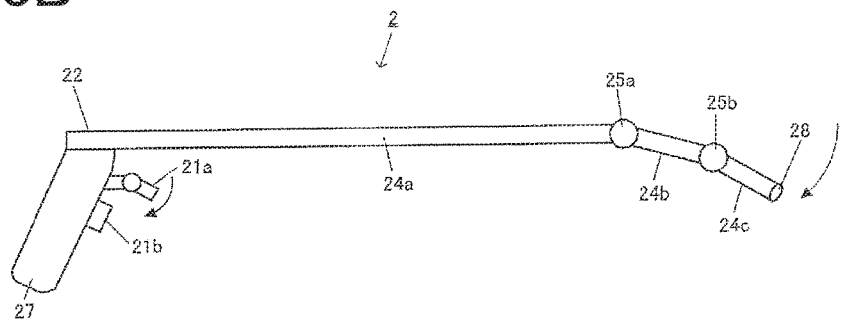

FIGS. 13A and 13B are illustrative of the construction and control configuration of the endoscope according to another embodiment of the invention. While the endoscope 2 according to the aforesaid embodiment is designed to use one moving joint 25 to vary the imaging direction (axis of sighting) of the imaging unit 28 as explained with reference to FIGS. 4A and 4B, it is to be appreciated that the endoscope 2 shown in FIGS. 13A and 13B is embodied in such a way as to include two moving joints 25a and 25b that are movable in a plurality of positions. As depicted in FIG. 13A, a first shaft 24a and a second shaft 24b are connected together in such a way as to be rotatable about the first moving joint 25a, and the second shaft 24b and a third shaft 24c are connected together in such a way as to be rotatable about the second joint 25b. An imaging unit is mounted on the distal end of the third shaft 24c. Operation of a direction input part 21a permits for rotation of the first moving joint 25a and the second moving joint 25b to vary the axis-of-sighting direction of the imaging unit 28. Rotational control of the first 25a and the second joint 25b may be individually implemented at varying direction input parts.

Figure 14A:
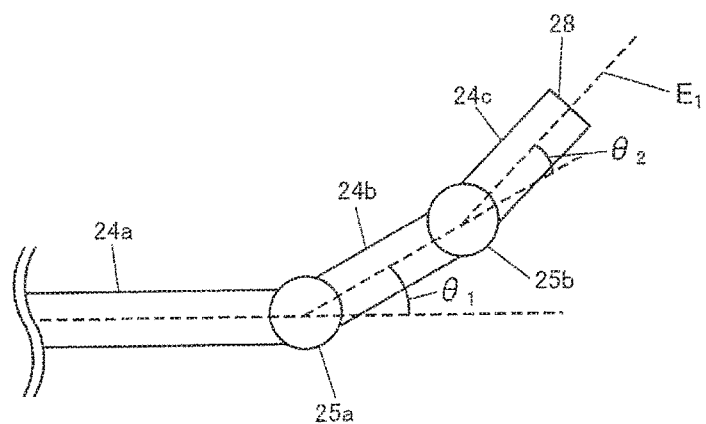
FIGS. 14A and 14B are illustrative of the actuation upon distance measurement of the endoscope according to one embodiment of the invention.
Figure 14B:
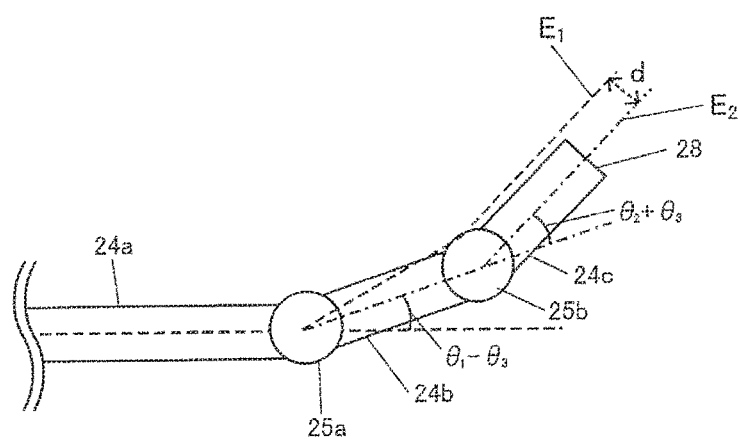

With the endoscope 2 including the moving joints 25a and 25b that are movable in such plural positions, the axis of sighting of the imaging unit 28 may be varied as set out just below in distance-measurement processing. FIGS. 14A and 14B are illustrative of how the operation of the distal end part of the endoscope 2 explained with reference to FIGS. 13A and 13B is controlled upon distance-measurement processing. FIG. 14A shows a state of the distal end part just before the start of distance-measurement processing, in which state the second shaft 24b is tilting at a joint angle θ1 of the first moving joint 25a with respect to the first shaft 24a, and the third shaft 24c is tilting at a joint angle θ2 of the second moving joint 25b with respect to the second shaft 24b.

As a distance-measurement instruction is entered in the state of FIG. 14A, it causes the controller 3 to rotate the first moving joint 25a and the second moving joint 25b as shown in FIG. 14B on the basis of an amount of distance-measurement control. In this example, the amount of distance-measurement control is set at θ3 so that the first moving joint 25a is adjusted to a position from which θ3 is subtracted and the second moving joint 25b to a position to which θ3 is added. Therefore, the axes of sighting of the imaging unit 28 will move parallel by a distance d (corresponding to the parallax) as indicated by an axis of sighting E1 and an axis of sighting E2. As the first image is taken in the state of the axis of sighting E1 and the second image is taken in the state of the axis of sighting E2, it causes the coordinate systems at the time when both the images are taken to match substantially or get parallel. This dispenses with the pseudo-stereoscopic distance-measurement principle for rotating systems as explained with reference to FIG. 12, easing off burdens on position computation processing and preventing errors occurring from rotation correction processing. Note here that such parallel movement of the axes of sighting may be implemented not just by use of plural moving joints but also in other various forms.

Figure 15A:
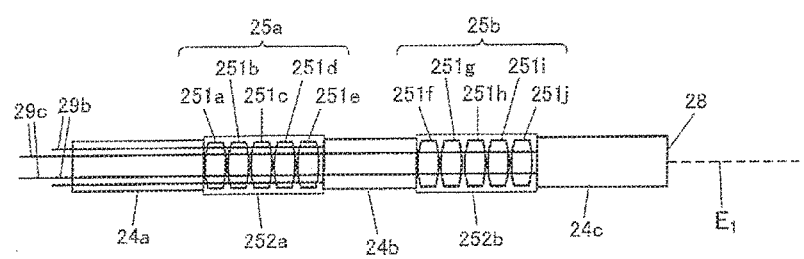
FIGS. 15A and 15B are illustrative of the construction and control configuration of the endoscope according to another embodiment of the invention.
Figure 15B:
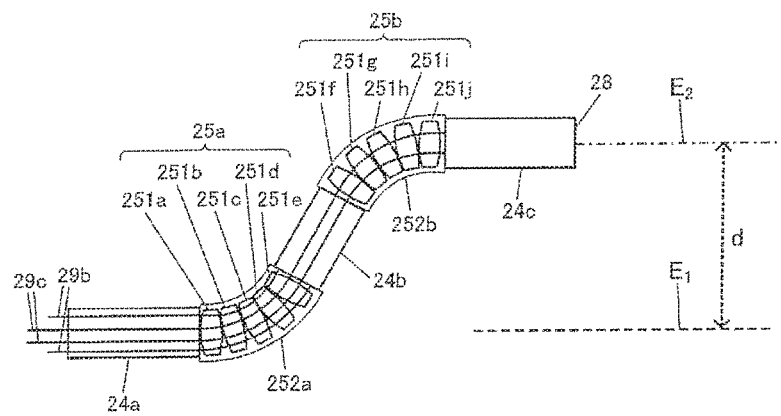

While the two moving joints 25a and 25b, each rotatable about the center axis, are explained with reference to FIGS. 14A and 14B, it is to be appreciated that the moving joint 25 may take various forms. FIGS. 15A and 15B are illustrative of the construction and control configuration of the endoscope according to a further embodiment of the invention. In the embodiment described herein, two moving joints 25a and 25b are used as in FIGS. 14A and 14B, but they have different arrangements. Here take the first moving joint 25a as an example. The first moving joint 25a includes, and is made up of, a plurality of articulating pieces 251a to 251d inside. Each articulating piece 251a to 251d is configured such that it is thicker in the vicinity of the center and gets thinner with a distance from the center. Such articulating pieces 251a to 251d are joined together whereby the first moving joint 25a is bendable as shown in FIG. 15B. The first moving joint 25a and the second moving joint 25b are provided with protective parts 252a and 252b (each formed of a rubber film as an example). The protective parts 252a and 252b conform in shape with the associated moving joints 25a and 25b depending on their moving state thereby preventing ingress of moisture inside or deposition of dirt.

The rotation (bending) of the first moving joint 25a may be controlled by pulling control wires 29b fixed to the second shaft 24b side by way of the driver 22. As any one of the control wires 29b shown is pulled, it causes the second shaft 24b to be bent in the direction of the pulled wire 29b. While there are two control wires 29b shown in the form of a plane view, it is to be appreciated that more control wires 29b are required so as to achieve three-dimensional bending. The same goes for the second moving joint 25b: the rotation of the third shaft 24c may be controlled by pulling a control wire 29c.

In such arrangement too, the axes of sighting may be moved parallel as in FIGS. 14A and 14B. As the first moving joint 25a and the second moving joint 25b are rotated from the state of FIG. 15A to the state of FIG. 15B, it permits for parallel movement of both the axes of sighting E1 and E2, which in turn gives rise to a parallax d between E1 and E2. While the parallax d is exaggeratedly shown in FIGS. 15A and 15B for the purpose of explaining the operation of each moving joint 25a, 25b, it is to be noted that the parallax d may be kept small by decreasing the amount of rotation of each moving joint 25a, 25b in the distance-measurement processing.

In the control flowchart explained with reference to FIG. 10, the timing of when the second image is taken is set at the time when the moving joint 25 is rotated by the amount of distance-measurement control. However, for instance, in the control using the control wire 29 explained with reference to FIGS. 15A and 15B, it is to be noted that there might possibly be a time lag between the driving operation of the driver 22 (pulling of the control wire 29) and the operation of the moving joint 25. How to determine the image for distance measurement (the second image) according the embodiment described herein is shown in FIGS. 16A and 16B.

FIG. 16A is illustrative of how images are taken in the vicinity of the distal end part of the endoscope 2 upon distance-measurement processing. Referring to four states shown in FIG. 16A, FIG. 16B shows images P1 to P4 taken upon distance-measurement processing. Note here that there is no need for displaying the images of FIG. 16B on the monitor 4. For an easy-to-understand explanation, reference is made to objects O1 and O2 that are being taken. As the moving joint 25 is rotated upon distance-measurement processing, it will cause the objects O1 and O2 to move relative to the already taken image, giving rise to an optical flow between the taken images. In a state where the moving joint 25 reaches the amount of distance-measurement control, the amount of rotation of the moving joint 25 becomes small, so does the optical flow, or it otherwise reaches 0 (equilibrium).

In the embodiment described herein, such inter-image characteristics are used to process a plurality of images taken during the rotation of the moving joint 25 upon distance-measurement processing. It is thus possible to determine the second image best for distance measurement, i.e., an image at the time when the moving joint 25 is rotated by the amount of distance-measurement control. In the example of FIGS. 16A and 16B, there is restoration processing carried out in which the moving joint 25 is restored back to the original state after rotated depending on the amount of distance-measurement control. To this end, the image P3 in equilibrium where the optical flow is zero is determined as the second image. By selection of the second image used for distance measurement out of a plurality of images taken upon distance-measurement processing, it is thus possible to get control over a time lag derived from the driver system for the moving joint 25 or the like. In turn, this enables the second image in the state rotated by the amount of distance-measurement control to be acquired with higher precision, resulting in improvements in precision with which distance is computed.

In the control flowchart explained with reference to FIG. 10, presume that the predetermined value, i.e., data stored in the memory 32 of the controller 3 are employed as the amount of distance-measurement control used for distance-measuring processing. In the distance-measurement processing by the endoscope 2, there might possibly be a change in the distance to the subject of interest. In the embodiment described herein, the amount of distance-measurement control is adjusted depending on an already known rough distance to the subject of interest so much so that the precision of an actual distance measurement can be improved.

With reference to the schematic view of FIG. 3, relations of the distance Z to the subject of interest to the parallax d are now explained. The distance Z to the subject of interest may be represented by Equation (1) explained with reference to FIG. 3. Let XL−XR=Xm. Equation (1) is rewritten as $$Z=d\cdot f/Xm \quad (1)'$$

Transformation with respect to Xm gives Equation (2)

$$Xm=d\cdot f/Z \quad (2)$$

Equation (2) teaches that with the (parallax) d fixed, the longer the distance Z, the smaller Xm is: because XL−XR gets small, the precision with which distance computation is implemented by applying image processing to the taken image would go low. By setting the parallax d at a large value in the case where there is a large Z, it is thus possible to improve the precision with which distance is computed. When there is a small distance Z, on the other hand, there is little loss of the precision with which distance is computed by setting the parallax d at a small value, and the parallax d can be smaller so that the amount of rotation of the moving joint 25 upon distance-measurement processing becomes smaller and the time taken by distance-measurement processing gets shorter.

Figure 17:
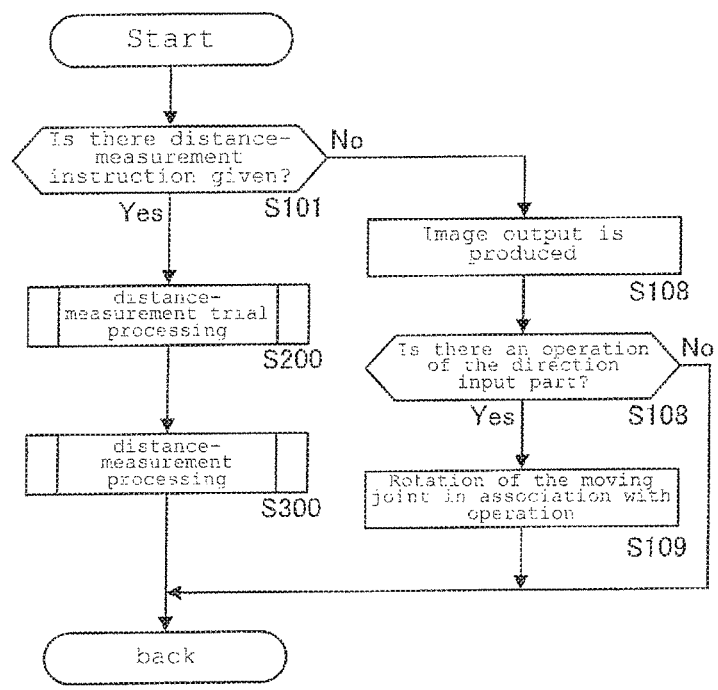
FIG. 17 is a control flowchart for the medical system according to another embodiment of the invention.
Figure 18:
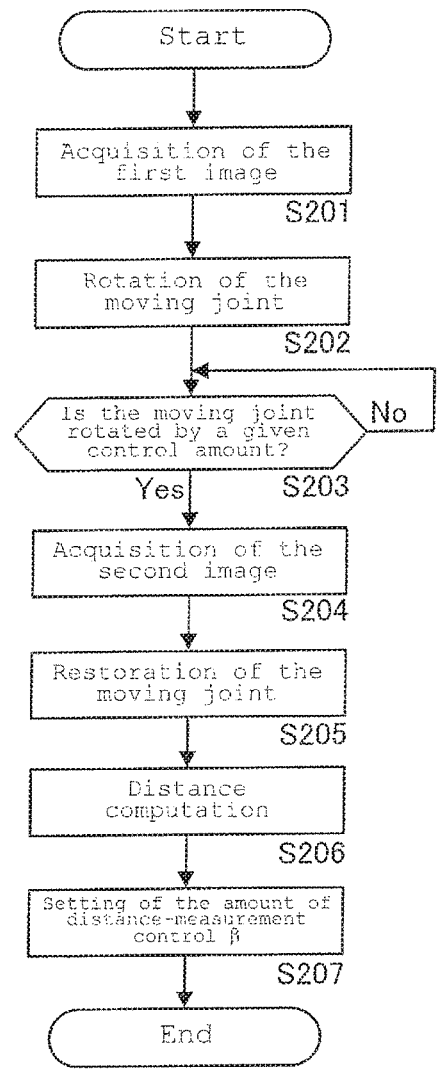
FIG. 18 is a flowchart for distance-measurement trial processing according to one embodiment of the invention.
Figure 19:
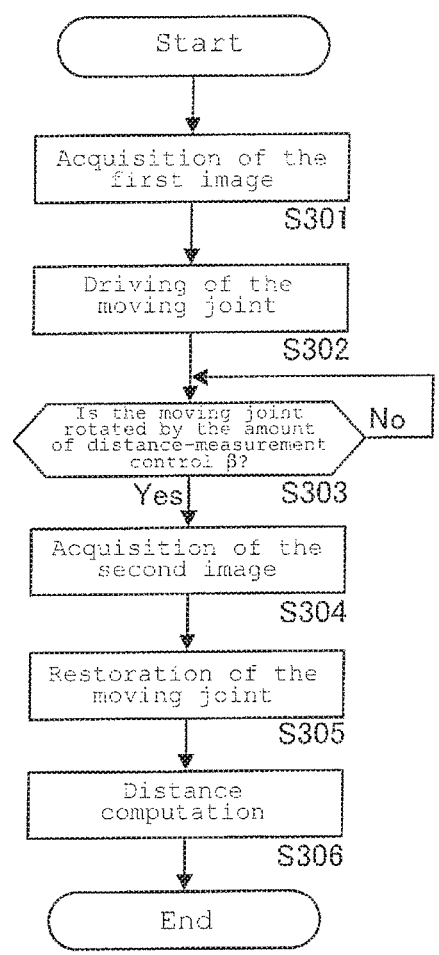
FIG. 19 is a flowchart for distance-measurement processing according to one embodiment of the invention.

FIGS. 17, 18 and 19 are control flowcharts for the endoscope system in the case where there is a variable amount of distance-measurement control. The distance-measurement instruction shown in FIG. 17 (S101) and the normal processing steps (S107, S108 and S109) of the endoscope 2 will not be explained because of being similar to those in the control flowchart explained with reference to FIG. 10. In the embodiment described herein, as the distance-measurement instruction (S101: Yes) is entered, distance-measurement trial processing (S200) is implemented prior to distance-measurement processing (S300) for computation of an actual distance. In the embodiment described herein, a rough distance to the subject of interest is computed in this distance-measurement trial processing (S200) thereby determining the amount of distance-measurement control used in the distance-measurement processing (S300). The amount of distance-measurement control may be determined not only by such distance-measurement trial processing (S200) but also on the basis of the distance measured by the previous distance-measurement processing. Alternatively, the amount of distance-measurement control may be determined by distance-measurement trial processing using an infrared sensor, an ultrasonic sensor or other like sensor mounted on the distal end of the endoscope 2.

FIG. 18 is a flowchart for the distance-measurement trial processing (S200) according to the embodiment described herein. As the distance-measurement trial processing (S200) gets started in response to a distance-measurement instruction (S101: Yes) entered, the first image is taken by the imaging unit 28 (S201). In S202, the controller 3 starts to rotate the moving joint 25 by the predetermined control amount (S202). As the moving joint 25 is found to be rotated by the predetermined control amount (S203: Yes), it allows for taking and acquisition of the second image (S204), followed by implementation of restoration processing to restore the moving joint 25 back to its original state (S205). Then, on the basis of the first image acquired in S201 and the second image acquired in S204, a distance to a (representative) position common to both the images is computed (S206), followed by the determination of the amount of distance-measurement control β on the basis of the computed distance (S207).

FIG. 19 is illustrative of the distance-measurement processing (S300) using the amount of distance-measurement control β set in this distance-measurement trial processing (S200). As the distance-measurement processing (S300) gets started, the first image is taken by the imaging unit 28 (S301). In S302, the controller 3 starts to rotate the moving joint 25 (S302) based on the amount of distance-measurement control β set in the distance-measurement trial processing (S200). As the moving joint 25 is found to be rotated by the amount of distance-measurement control β (S303: Yes), the second image is taken (S304), and the moving joint 25 is restored back to its original state (S305). Then, on the basis of the first image taken in S301 and the second image taken in S304, a distance to the subject of interest is computed (S306). With the distance-measurement trial processing according to the embodiment described herein, it is thus possible to bring up the precision with which the distance to the subject of interest is computed in the distance-measurement processing.

While the endoscope system including the endoscope 2 and controller 3 has been explained, it is to be noted that the endoscope system according to the embodiment described herein further includes in the trocar 1 a trocar sensor 12 capable of detecting various states of the endoscope 2, as explained with reference to FIG. 8, etc. As described just below, the embodiment described herein includes a trocar sensor 12 or the like that is capable of detecting various states of the endoscope 2. Note here that the invention disclosed herein is not limited to the trocar sensor 12; various modes capable of detecting various states of the endoscope 2 such as the provision of an acceleration sensor on the endoscope 2 side may be relied up.

The distance-measurement processing steps (S102 to S106) explained with reference to FIG. 10 are based on the assumption that there is no movement but the rotation of the moving joint 25. In actual applications, however, the endoscope 2 may possibly shake or otherwise rock during the distance-measurement processing because it is operated while the gripper member 27 is grasped by the operator. In the embodiment described herein, various pieces of information produced out of the trocar sensor 12 are used and the amount of movement of the imaging unit 28 measured during the distance-measurement processing is used. While taking into consideration the amount of movement of the endoscope 2 between a point of time when the first image is taken and a point of time when the second image is taken, distance computation is carried out in the distance-measurement processing thereby improving the precision of the computed distance. When the trocar sensor 12 is used as the sensor, various states of the endoscope 2 to be detected include a tilt angle detected by the tilt angle detection sensor 121, an amount of advanceable/retractable movement detected by the amount-of-advanceable/retractable-movement detection sensor 122, and an amount of rotation detected by the amount-of-rotation detection sensor 123. Such various states are used to acquire the amount of movement of the endoscope 2 resulting from shaking or rocking during the distance-measurement processing, i.e., the amount of movement of the imaging unit 28, and with that amount in consideration, distance computation can be carried out to bring the precision up.

In the embodiment of detecting various states of the endoscope 2 by making use of a sensor such as the trocar sensor 12, there may be such possible distance-measurement processing implemented as explained below. FIGS. 20A and 20B are illustrative of distance-measurement processing that is implemented in follow-up imaging processing using the trocar sensor 12. The follow-up imaging processing is designated and implemented by the operator or the like for rotation of the moving joint 25 without recourse to the operation of the direction input part 21a unlike the normal processing for rotation of the moving joint 25 in response to the operation of the direction input part 21a.

In the embodiment described herein, a reference surface St that is defined by the surface of the affected site is set on a follow-up reference surface, and the moving joint 25 is driven and controlled such that the axis of sighting of the imaging unit 28 is at a given angle (here at an orthogonal angle) with respect to that reference surface St. The direction of axis of sighting of the imaging unit 28 is determined on the basis of a sensor signal produced out of the trocar sensor 12. Note here that in FIGS. 20A and 20B, a sign θb stands for an angle that the first shaft 24a forms with a reference coordinate system C, a sign θj indicates a control angle of the moving joint 25 in the follow-up processing, and P1 and P2 stand for points of intersection of the direction of axis of sighting of the imaging unit 28 with the reference surface St.

When there is a movement of the endoscope 2 from the state of FIG. 20A to the state of FIG. 20B, the direction of axis of sighting of the imaging unit 28 is maintained orthogonally to the reference surface St in either case. On the basis of a sensor signal detected by the trocar sensor 12, the controller 3 determines a direction in which the first shaft 24a turns to rotate the moving joint 25 by the driver 22 such that the direction of axis of sighting of the imaging unit 28 is set at a given angle (here an orthogonal angle) with respect to the reference surface St. While the operation of the moving joint 25 is explained in the form of a two-dimensional movement on the sheet plane with reference to FIGS. 20A and 20B, it is to be understood that the follow-up imaging processing is also well compatible with a three-dimensional movement including a direction orthogonal to the sheet plane.

Referring to the control configuration of FIG. 9, as the follow-up mode is designated in the mode input part (not shown) of the input unit 21, it permits the controller 3 to implement the follow-up imaging processing for controlling the driver 22 on the basis of a sensor signal produced out of the trocar sensor 12 instead of control of the driver 22 (angle adjustment of the moving joint 25) on the basis of an operating signal from the direction input part 21a. Referring here to the memory 32 of the controller 3, the follow-up reference surface set on the reference coordinate system is stored, and the driver 22 is controlled in the follow-up imaging processing such that on the basis of the sensor signal and follow-up reference surface, the imaging unit 28 of the endoscope 2 has a given angular relation to the follow-up surface.

Referring to the follow-up reference surface used for the follow-up imaging processing, the input unit 21 may include an setting input part through which the follow-up reference is set by the operation of the operator or, alternatively, the follow-up reference surface may be set on the basis of the results of detection by various sensors such as images taken by the endoscope 2. In this control configuration, the surface of the affected site is set on the reference surface St; however, the reference surface may be a virtual one rather than a real one. Further, the imaging unit 28 may be set at a given tilt angle rather than the orthogonal angle with respect to the reference surface St. Still further, the reference surface St may be a curved one rather than the plane. For instance, the curved surface of the affected site taken by another endoscope inserted through the interior of the patient's body apart from the medical instrument 2 may be set as the reference surface St.

In such follow-up imaging processing, for instance, the distance from the imaging unit 28 to the reference surface St may be computed using the amount of movement between the first image taken in the state of FIG. 20A and the second image taken in the state of FIG. 20B, and between FIGS. 20A and 20B acquired by the trocar sensor 12. In this processing, there may be distance computation implemented in which the first image is taken at the time when the distance-measurement instruction is entered, and the second image is taken under the conditions that the endoscope 2 moves from the first image by the predetermined amount of movement. Alternatively, there may be distance computation implemented in which the first image is taken at the time when the distance-measurement instruction is entered, and the second image is taken after the elapse of a given time to sense the amount of movement of the endoscope 2 in a time period from the acquisition of the first image to the acquisition of the second image.

In any control configuration, the distance to the subject of interest is computed using the first image and the second image, and the amount of movement of the endoscope 2 between at the times when both the images are acquired. In the distance-measurement processing at the time of such follow-up imaging processing, it is possible to implement distance computation with higher precision at the time of distance-measurement processing because the axes of the imaging unit 28 are kept parallel with each other before and after the movement of the endoscope 2. Unlike the aforesaid distance-measurement processing, there is no need for rotating the moving joint 25 for distance-measurement processing, so that a succession of images taken by the imaging unit 28 can continuously be viewed on the monitor 4.

Figure 21:
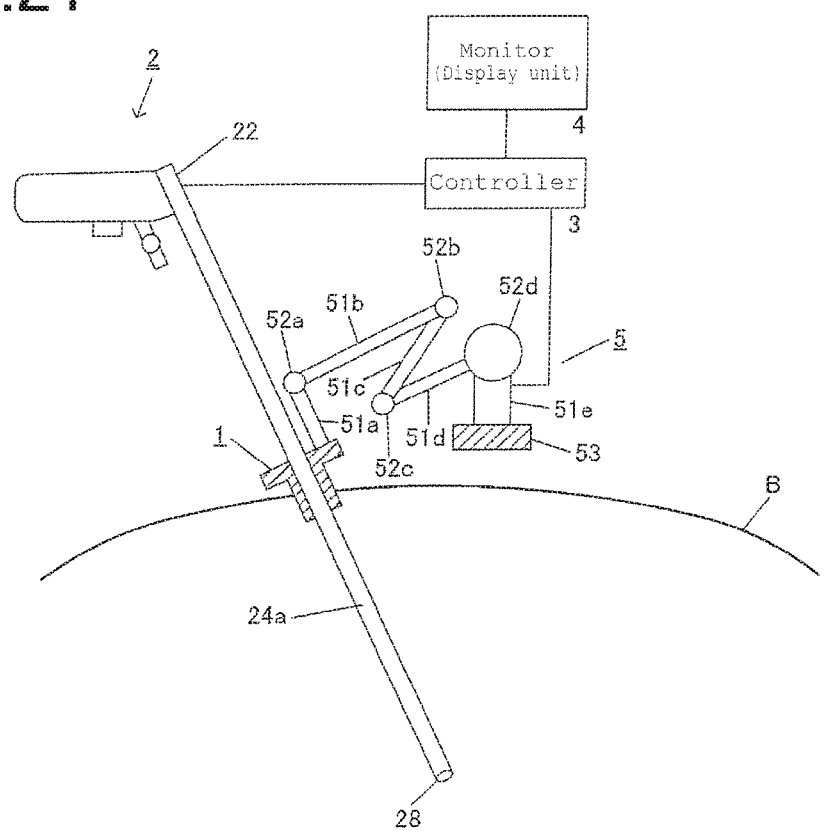
FIG. 21 is illustrative of how the interior of the body is viewed using the medical system according to another embodiment of the invention.

While some embodiments having the moving joint located in the interior of the patient's body as shown in FIG. 8 have so far been described, it is to be noted that the moving joint may be located externally of the body. FIG. 21 shows an embodiment wherein there is the moving joint located outside the body. In the endoscope system according to the embodiment described herein, the endoscope 2 does not include any moving joint, and instead include a trocar position control unit 5 for making the position of the trocar 1 variable. This trocar position control unit 5 includes a base 53 placed on the floor surface lying outside the body, etc., a plurality of arms 51a to 51e, and a plurality of moving joints 52a to 52d for making a rotatable connection between the adjacent ones of the arms 51a to 51e. The moving joints 52a to 52d are each capable of rotation by a driver such as a motor. The driver adapted to rotate each of the moving joints 52a to 52d is driven by control of the controller 3.

In the endoscope system shown in FIG. 21, the trocar 1 may be rotated about a point of insertion of the trocar 1 (a position on the body surface B through which the trocar 1 is to be inserted) by control by the trocar position control unit 5, and operated while being less invasive of the body surface B of the patient. The controller 3 controls the trocar position control unit 5 to rotate the trocar 1 about the point of insertion of the trocar 1 so that there is a change in the angle of insertion of the endoscope 2, which in turn causes a change in the direction of axis of sighting of the imaging unit 28 mounted on the distal end of the endoscope 2. In the endoscope system according to the embodiment described herein, too, it is thus possible to rotate the moving joints 52a to 52d for movement of the axis of sighting of the endoscope 2 as is the case with the aforesaid embodiments. With the amount of control of the moving joints 52a to 52d in the trocar position control unit 5, it is possible to acquire the tilt angle, amount of advanceable/retractable movement and amount of rotation of the endoscope 2. The distance to the subject of interest may be computed on the basis of the amount of distance-measurement control depending on the thus acquired tilt angle, amount of advanceable/retractable movement and amount of rotation of the endoscope 2, the first image taken before the implementation of movement processing and the second image taken during the implementation of movement processing.

While the embodiments according to some aspects of the invention have been described, it is to be appreciated that the invention is in no sense limited to them, and that embodiments obtainable from combinations of them are encompassed in the category of the invention too.

REFERENCE SIGNS LIST

1: Trocar
111: Upper housing
112: Lower housing
113: Cylindrical tube
114: Cable
115: Insertion path
116: Coupler member
12: Trocar sensor
121: Tilt angle detection sensor
122: Amount-of-advanceable/retractable-movement detection sensor
122a: Amount-of-advanceable/retractable-movement detection roller
122b: Photosensor
123: Amount-of-rotation detection sensor
123a: Amount-of-rotation detection roller
123b: Photosensor
13: Communication unit
2: Medical instrument (endoscope)
2': Medical instrument (forceps)
21: Input unit
21a: Direction input part
21b: Distance-measurement instruction part,
22: Driver
24a: First shaft
24b: Second shaft
24c: Third shaft
25: Moving joint
25a: First moving joint
25b: Second moving joint
26: Distal-end gripper member (end effector)
28: Imaging unit
3: Controller
31: Control unit
32: Memory
4: Monitor
5: Trocar position control unit
51a to 51e: Arms
52a to 52d: Moving joints
53: Base

The invention claimed is:

1. A control method of measuring distance by an endoscope, the control method being carried out by a controller, the method comprising:
acquiring a first image being imaged at a first visual axis by an image sensor disposed on a distal side of the endoscope;
moving a joint of the endoscope so that the image sensor can acquire a second image at a second visual axis being angled a predetermined angle with regards to the first visual axis;
acquiring the second image being imaged at the second visual axis by the image sensor;
moving the joint so that the image sensor can image at the first visual axis;
computing a distance between the image sensor and a subject of interest of the first image based on both the first image and the second image; and
updating the predetermined angle based on the distance between the image sensor and the subject of interest.

2. The control method of measuring distance by an endoscope according to claim 1, wherein the second image is determined from a plurality of images being imaged between the first visual axis and the second visual axis by the image sensor.

3. The control method of measuring distance by an endoscope according to claim 1, further comprising:
acquiring an amount of movement of the endoscope in a longitudinal direction of the endoscope;
wherein the computing of the distance between the image sensor and the subject of interest of the first image is based on the first image, the second image and the amount of movement of the endoscope.

4. The control method of measuring distance by an endoscope according to claim 1, wherein the joint comprises a plurality of joints.

* * * * *